(12) United States Patent
Gong (10) Patent No.: US 8,743,352 B2
(45) Date of Patent: Jun. 3, 2014

(54) COAXIAL ILLUMINATION OF COULTER APERTURE IN FULL FUNCTION HEMATOLOGY ANALYZER

(76) Inventor: Weiyan Gong, Atlanta, GA (US)

( * ) Notice: Subject to any disclaimer, the term of this patent is extended or adjusted under 35 U.S.C. 154(b) by 485 days.

(21) Appl. No.: 12/860,166

(22) Filed: Aug. 20, 2010

(65) Prior Publication Data

US 2011/0254533 A1    Oct. 20, 2011

Related U.S. Application Data

(60) Provisional application No. 61/283,679, filed on Dec. 8, 2009.

(30) Foreign Application Priority Data

Apr. 19, 2010    (CN) .......................... 2010 1 0142501

(51) Int. Cl.
*G01N 33/48* (2006.01)
*G01N 15/02* (2006.01)
*G01N 21/00* (2006.01)

(52) U.S. Cl.
USPC .............................. 356/39; 356/336; 356/337

(58) Field of Classification Search
None
See application file for complete search history.

(56) References Cited

U.S. PATENT DOCUMENTS

| | | | | |
|---|---|---|---|---|
| 3,453,438 A | * | 7/1969 | Ban et al. .......................... 377/12 |
| 3,675,768 A | * | 7/1972 | Legorreta-Sanchez ........... 209/4 |
| 3,738,759 A | * | 6/1973 | Dittrich et al. ................ 356/442 |
| 3,740,149 A | * | 6/1973 | Whetten ........................ 356/335 |
| 3,740,553 A | * | 6/1973 | Whetten ........................ 250/292 |
| 3,770,349 A | * | 11/1973 | Legorreta-Sanchez ......... 356/73 |
| 3,910,702 A | * | 10/1975 | Corll ................................ 356/72 |
| 4,014,649 A | * | 3/1977 | Kiesow ........................... 436/68 |
| 4,198,160 A | * | 4/1980 | Kachel et al. ................... 356/72 |
| 4,280,623 A | * | 7/1981 | Legorreta ....................... 209/3.1 |
| 4,341,993 A | * | 7/1982 | Brunsting et al. .............. 377/10 |
| 4,426,154 A | * | 1/1984 | Steen ............................... 356/73 |
| 4,751,188 A | * | 6/1988 | Valet ............................... 436/63 |
| 5,125,737 A | * | 6/1992 | Rodriguez et al. .............. 356/39 |
| 5,194,909 A | * | 3/1993 | Tycko .............................. 356/40 |
| 5,616,501 A | * | 4/1997 | Rodriguez et al. .............. 436/63 |
| 6,426,615 B1 | * | 7/2002 | Mehta .......................... 324/71.4 |
| 6,624,621 B2 | * | 9/2003 | North, Jr. ..................... 324/71.4 |
| 6,646,742 B1 | * | 11/2003 | Gangstead et al. ............ 356/342 |
| 7,586,604 B2 | * | 9/2009 | Sharpe et al. ................. 356/338 |
| 2004/0080747 A1 | * | 4/2004 | Cerni et al. ................... 356/338 |
| 2007/0146704 A1 | * | 6/2007 | Schmidt et al. ............... 356/338 |
| 2010/0231909 A1 | * | 9/2010 | Trainer .......................... 356/336 |

FOREIGN PATENT DOCUMENTS

JP    2003057230 A    *    2/2003

* cited by examiner

*Primary Examiner* — Gordon J Stock, Jr.
(74) *Attorney, Agent, or Firm* — Oakwood Law Group, LLP; Yuchien Wei (57) ABSTRACT

A method for directly illuminating a Coulter aperture so light scattering can be incorporated into the classical Coulter aperture and 3-diff blood analyzer to realize full functional hematology analyzer by providing a flow chamber which is separated into two portions by a plate having a Coulter aperture; and using a light source to directly coaxial illuminate the Coulter aperture wherein the illuminating beam propagates in the same direction as the axis of the Coulter aperture and the cell's moving direction.

38 Claims, 8 Drawing Sheets

FIG. 7 coaxial illumination
FIG. 8B cross illumination
FIG. 8A

COAXIAL ILLUMINATION OF COULTER APERTURE IN FULL FUNCTION HEMATOLOGY ANALYZER

REFERENCE TO RELATED APPLICATIONS

This patent application claims the benefit of U.S. Provisional Application No. 61/283,679 filed on Dec. 8, 2009.

BACKGROUND OF THE INVENTION

1. Field of the Invention

The present invention generally relates to the field of medical screening and diagnostic hematology instruments which performs complete blood count (CBC), white blood cell 3 part differential and other blood parameter measurements for humans, or similar analysis for other cells, or similar analysis for animal blood, or similar analysis of material components that have requirements for its particle contents and size—such as food, beverage, cosmetics, pharmaceutical or petroleum with a need to test the purity of said substance. More particularly, the invention relates to the methods and instruments for differentiating and identifying subpopulations of leukocytes in a blood sample by using Coulter impedance and light scattering only, especially by using backscattering signals through the new innovative invention of direct coaxial illumination of the Coulter aperture.

2. Background of the Invention

Human blood consists of plasma (approximate 58%) and cellular elements (approximate 42%). The cellular elements include red blood cells (RBC, 4-5 millions per microliter), white blood cells (WBC, 5-9 thousands per microliter), and platelets (PLT, 200-400 thousands per microliter). The WBC primarily have 5 subpopulations: Neutrophils (phagocytosis and proteolysis), Basophils (Inflammation and allergic reactions), Eosinophils (Viral infection), Monocytes (Phagocytosis) Lymphocytes (Including B cells and T cells, function in humoral immunity).

The counting and sizing of RBCs, the counting of WBCs, and counting of platelets is referred to as a complete blood count (CBC). The separation of white blood cells into the five major subpopulations and their quantification on a percentage basis is referred to as a five-part differential (5-diff).

Before 1950 blood cell counts by manual counting used the hemocytometer. The era of automated cell counting was introduced by Wallace H. Coulter in the early 1950's. The Coulter Principle, the electronic method of counting and measuring the size of microscopic particles and named for its inventor Wallace H. Coulter, states that a particle pulled through an orifice (aperture), concurrent with an electrical current, will produce a change in impedance that is proportional to the size of the particle traversing the orifice. This impedance change creates an electric pulse and is commonly referred to as a DC (direct current) signal. The related U.S. Pat. No. 2,656,508 to Coulter was issued Oct. 20, 1953. Although more than half century has passed the Coulter principle and Coulter aperture continue to be used in all hematology blood analyzer today and the DC signal still is the indispensible signal among others. Today ninety-eight percent of CBCs are performed on instruments using the Coulter Principle.

Automated counting increased the sample size of the blood test 100 times more than the usual manual microscope method by counting in excess of 6000 cells per second. Additionally, it decreased the time it took to analyze from 30 minutes to fifteen seconds and reduced the error by a factor of approximately 10 times.

Figure 1:
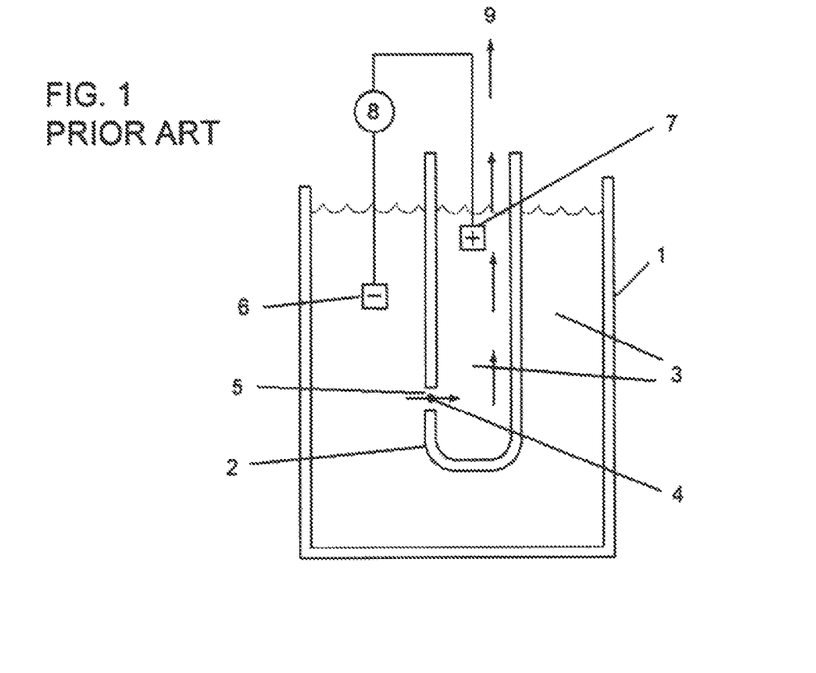
FIG. 1 shows the Coulter Principle and Coulter Aperture.

The Coulter Principle states that particle suspension in a weak electrolyte solution of two chambers, separating two electrodes, are connected by a small aperture. When the particles suspended in solution are drawn through the aperture, the particle displaces its volume of electrolyte and momentarily increasing the impedance of the aperture. The Coulter Principle used in impedance-based blood analyzer is schematically described in FIG. 1. The two Chambers, aperture bath 1 and aperture tube 2, are connected by only one path, the aperture 5. Suspended in saline solution 3, blood cell 4, one at a time, due to pressure difference of vacuum 9, passes through the aperture 5 and the impedance changes creates a pulse current 8 between two electrodes 6 and 7. The pulse (DC) is directly proportional to the volume of the cell that produces this pulse. Because Neutrophil, Basophil and Eosinophil have similar volume, by the impedance method, only three parts can be distinguished. Thus, three-part differential (3-diff) blood count can be obtained.

In order to obtain 5-diff, several techniques had emerged since the 90's. Light scattering, radio frequency and chemical dyeing were applied to hematology instruments to obtain five-part differential, and 5-diff hematology instruments available commercially since then. All these instruments are based the technology called flow cytometry.

Figure 2:
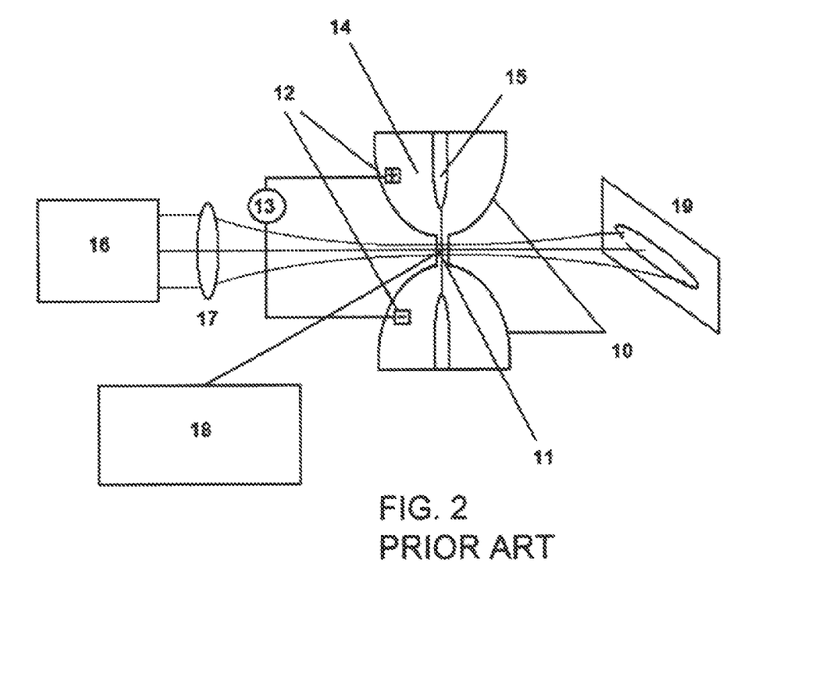
FIG. 2 illustrates the basic principle of the flow cytometry based light scattering blood analyzer.

The basic principle of the flow cytometry based on light scattering blood analyzer can be illustrated as FIG. 2. The two cones of flow cell 10 for the sheath flow 14, force sample flow 15 at the center of sheath flow to form hydrodynamic focusing. Two electrodes 12 and aperture current 13 create an impedance pulse when a cell passes through aperture 11. The laser source 16, through focusing lens 17 illuminates the aperture and creates the forward scattering (FLS) and axial light loss (ALL) detected by detector 19, and 90° side light scattering (SLS) (and fluorescence) detected by detector 18. Thus, when each cell passing the orifice, at least 3 signals can be detected, i.e. DC, FLS and SLS, if a radio frequency source is applied to the two electrodes 12, then another signal, called RF (radio frequency), will be available and RF is sensitive to cell internal contents.

Figure 3:
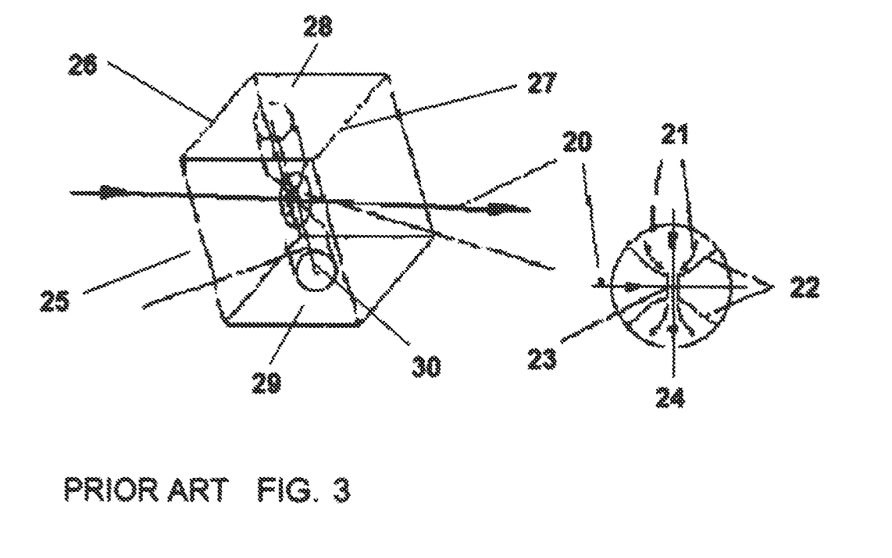
FIG. 3 is schematic diagram of flow cell.

RF is Wallace Coulter's another important invention and related U.S. Pat. No. 3,502,974 to Coulter was issued Mar. 24, 1970. FIG. 3 is a schematic diagram of flow cell. In the center of quartz rectangular prism 25, size about 4 mm×4 mm×8 mm, drill a through hole of diameter 50 μm, along its long axis 30. Two cones 22 were made by a special drilling grinding machine from opposite top surface 28 and bottom surface 29, aligned cone axis and roof to coincide with the 50 μm hole axis 30 until 50 μm orifice 23 about 70 μm long in the middle of the rectangular prism. Two cones 22 for the sheath flow 21 force the sample flow 24 in the center of orifice 23 to form a sample filament so that cell will passing through the orifice one at a time (hydrodynamic focusing). The focused laser beam 20 illuminates the cell in the sample flow. From FIG. 2 and FIG. 3 we can see that in the flow cytometry based instruments, the laser light beam propagates along the axis in the direction (horizontal in the FIGs) perpendicular to cell moving direction (vertical in the FIGs), which will be referred to as cross illumination in this paper to distinguish from the coaxial illumination presented in this invention, which will be described later.

All flow cytometry based light scattering hematology instruments in the world now are all using flow cell, hydrodynamic focusing and cross illumination. When a cell passes through an orifice and interacts with focused laser light, the light scattering signals are created and can be detected. Except forward light scattering (FLS), axial light loss (ALL), and 90° side light scattering (SLS) signals shown in FIG. 2, there will have back scattering light (BSL) which also can be detected. Although back scattering is proved more sensitive to particle's (cell's) internal content and structure (Kerker et al., 1979; Kerker, 1983; Mourant et al., 1998), its intensity is about 3 orders of magnitude weaker than forward scattering. When using flow cell as shown in FIG. 2 and FIG. 3, the focused laser beam will first hit flow cell's front surface 26, then hit the cylindrical surface of orifice 23, and finally hit the back surface 27, thus very strong reflected light creates unwanted background for back scattering detection. As Gangstead et al., pointed out in U.S. Pat. No. 6,646,742, "Unfortunately, using any of the available conventional flow cytometry illumination arrangements, the walls of these walled-conduit structures conventionally generates such an enormous quantity of background scatter noise". This is the one of the main technical bottleneck that no commercial hematology instrument is capable of incorporating backscattering for enhancing cell discrimination power purpose.

Several attempts were made using backscattering only in the laboratory, such as U.S. Pat. No. 6,743,634 B2 (Kramer, Jun. 1, 2004) and U.S. Pat. No. 6,869,569 B2 (Kramer, Mar. 22, 2005), all use a plurality of optical fibers and PMTs and are impossible of being incorporated into a practical commercial instrument due to its complex structure and cost.

Only this unique invention will make detection of cell's backscattering signal possible in a practical commercial hematology instrument for the first time in the hematology instrument history.

SUMMARY OF THE INVENTION

The present invention provides an innovative illuminating method, i.e. direct coaxial illuminating the Coulter Aperture in hematology instruments. The invention provides a kind of blood analyze instrument of directly illuminating Coulter aperture. It includes illuminating optics system, the flow chamber with optical windows, forward and back scattering signals detecting optics system. The present invention is characterized in coaxial illumination of Coulter aperture, i.e. the illuminating beam from a gas laser, a He—Ne laser, an Argon-ion laser, a diode laser, a fiber coupled diode laser, a solid state laser, a fiber coupled solid state laser, a diode pumped solid state laser, a tunable laser, a fiber laser, a light emitting diode (LED), an arc lamp, or an incandescent light source propagating in the same direction as the axis of Coulter aperture and cell's moving direction.

Coaxial illumination means that the illuminating light beam propagates in the direction coincident with axis of Coulter Aperture, or cell's moving direction (Coaxial), wherein the light source has different wavelengths for different applications. The wavelength of the light from the light source can range from ultraviolet to infrared. Using this unique illumination method, we can entirely get rid of high precision, complicated and costly flow cell (like one shown in FIG. 2 & FIG. 3), which is indispensable for conventional high-end flow cytometry based five-part differential blood analyzer. Unfortunately until now these kind instruments still dominate the world high-end blood analyzer market. Since no flow cell, the complicated, difficult operating and maintenance procedures for hydrodynamic focusing mechanism is eliminated in the new light scattering and impedance based blood analyzer. Except above advantages of reduce the cost and complexity, the most profitable advantage of the innovative illumination scheme is that the light scattering, especial the back light scattering, can be directly incorporated into conventional impedance based blood analyzer.

In the coaxial illumination the laser beam will be focused to the middle of Coulter aperture with focused waist little less than diameter of Coulter aperture and the Rayleigh region of the Gaussian beam will be several Coulter aperture lengths. The special designed detection system is optical, mechanical, electronic, opto-electronic, opto-mechanical or any combination and will ensure that the scattering signals come from the particles in only interested spatial region. The signal detection system is only sensitive to a cell within the spatial region and any reflected light background from any interface of different optical materials which is background noise will be blocked and only useful for back scattering light from a cell and can be detected to enhance the signal to noise ratio. The detection system can detect forward and back direction scattering light in different angular regions, or a combination of several angular regions. The signal detection system can detect single wavelength or multi-wavelength spectroscopic light in both forward and backward directions. Detectable light signals in both forward or backward directions can be single wavelength or multi-wavelength fluorescence signal, or other inelastic light scattering signals, such as Raman scattering or anti-stokes Raman scattering.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

FIGS. 11A, 11B and 11C are Oscilloscope displays of detected forward scattering (upper track) and DC (lower track) signal of 7 µm latex particle;

DETAILED DESCRIPTION OF PREFERRED EMBODIMENTS

In order to incorporate light scattering into impedance based blood analyzer, the first thing is to make the conventional flow chamber (i.e., WBC chamber or RBC chamber, or both) optically transparent so that illuminating light beam and scattering light can have their optical path.

Figure 4:
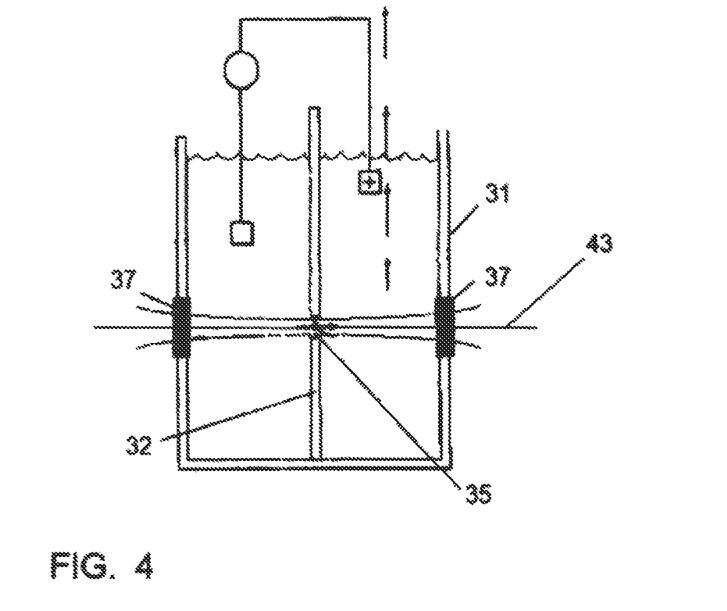
FIG. 4 shows the flow chamber with two parallel plate windows of optical glass, fused silica, sapphire, quartz.
Figure 5:
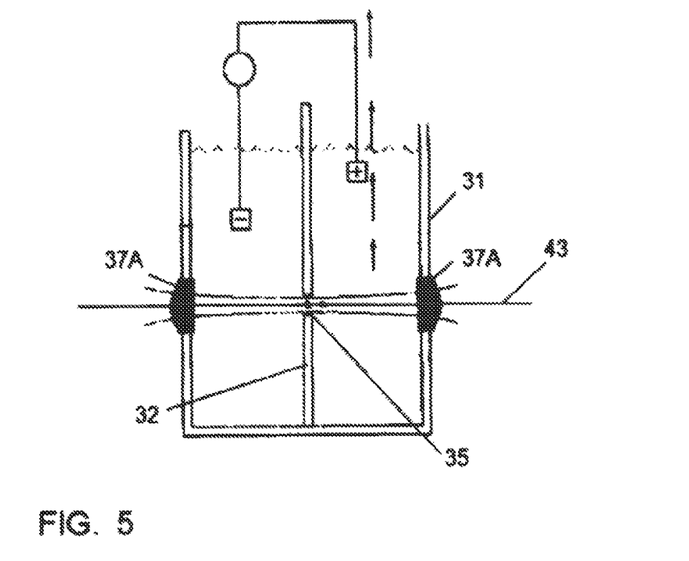
FIG. 5 is the same as FIG. 4 except that the two optical lenses are used as optical windows of the flow chamber.

Referring to drawings FIG. 4 and FIG. 5, the flow chamber is separated into two portions by aperture plate 32. The two portions of the chamber are connected by only one path, i.e. the Coulter aperture 35. Two optical windows, 37 (two parallel plates) in FIG. 4, or 37A (two optical lenses) in FIG. 5, inserted in the wall 31 of flow chamber, form an optical path for illumination and scattering detection. The two window's surfaces are centered at and perpendicular to common axis 43 of laser beam and Coulter aperture axis (also the cell's moving direction).

Figure 6:
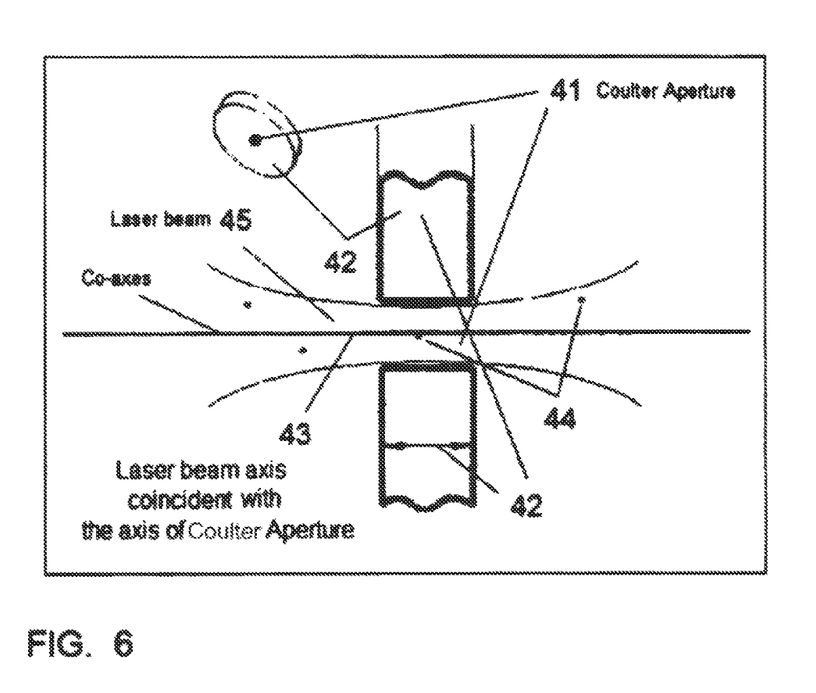
FIG. 6 is schematic diagram of Coaxial Illumination of the Coulter Aperture.
Figure 7:
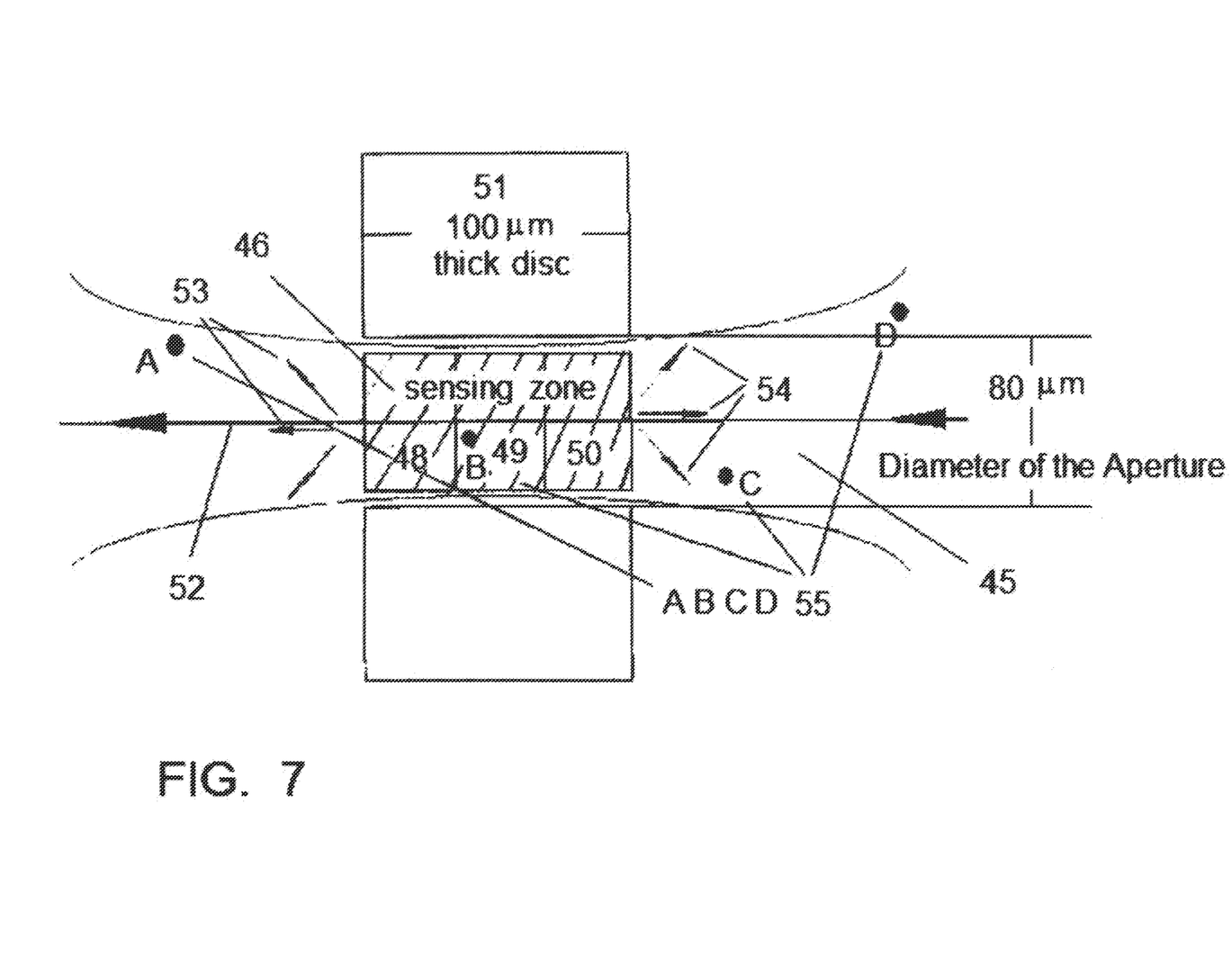
FIG. 7 illustrates the interrogation and sensing zone of Coaxial Illumination of the Coulter Aperture.

FIG. 6 and FIG. 7 illustrate the concept and realization of "Coaxial Illumination of Coulter Aperture". In FIG. 6 in the center of the aperture disc 42 (thickness of 100 µm) is the Coulter aperture 41 (diameter of 50 µm to 80 µm). Focused laser beam 45 propagates along the common axis 43 (Coaxial illumination) and interacts with cells 44. In FIG. 7 laser beam 45 is focused in the middle of Coulter aperture, also the sensing zone 46, and propagates from right to left along the common axis 52. The diameter of the aperture is 80 µm and the thickness 51 of aperture disc is 100 µm. The fiber coupled laser 80 through fiber 79 entering the focus optics 75 in FIG. 9 and FIG. 10. The focused laser beam is designed to have focused waist about 60 µm to 75 µm (little less than aperture diameter 80 µm) and to have Rayleigh region about several aperture lengths (thickness 51, 100 µm). The focus optics should be designed to meet above two criterions (waist size and Rayleigh region) so the aperture can be illuminated uniformly. The sensing zone 46 can be divided to 3 portions, front portion 50, middle portion 49, and rear portion 48. The cells 55 (A, B, C, D) (see FIG. 7) are all be interrogated with laser beam but only cell B within the sensing zone can be detected, by using the spatial discriminating gate (implemented optically, such as the special designed detection optical system showed in FIG. 9 and FIG. 10) and temporal discriminating gate (implemented electronically). The forward scattering light 53, traveling to left and back scattering light 54, traveling to right, then can be detected by detection optics 81 and 77, respectively in FIG. 9 and FIG. 10.

Figure 8A:
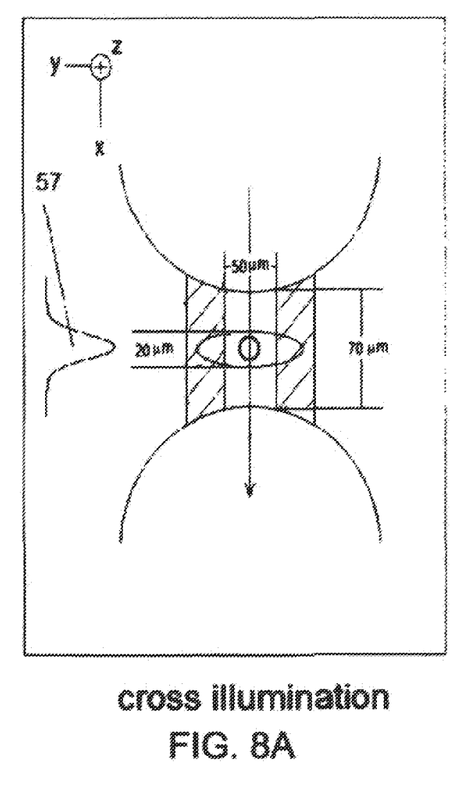
FIGS. 8A and 8B compares two illumination methods, left portion is conventional illumination arrangement (Cross illumination of flow cell) and right portion is the Coaxial illumination of the Coulter Aperture presented in this invention.
Figure 8B:
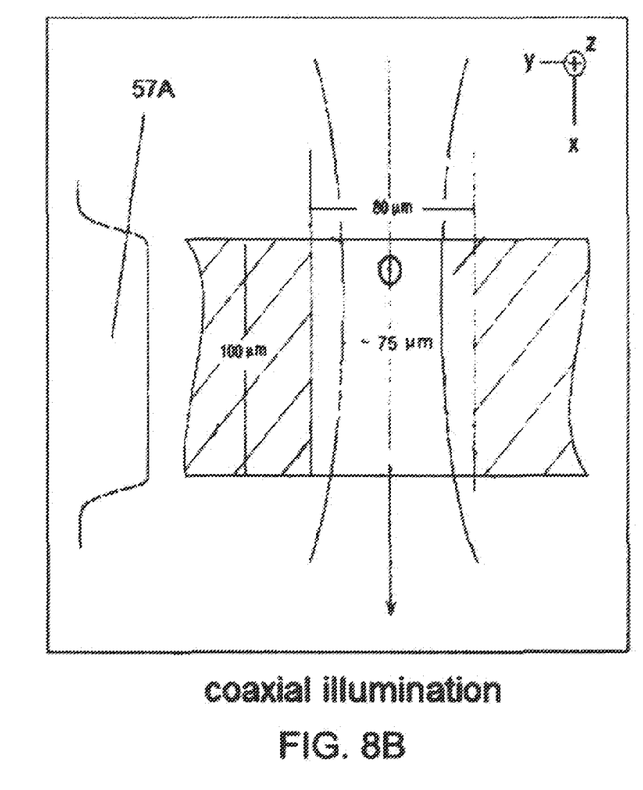

FIG. 8 compares two illumination methods, the left part of FIG. 8 is the available conventional flow cytometry illumination arrangement with walled-conduit structures flow cell, and is referred to as cross illumination because the illuminating laser beam propagating in the direction Y perpendicular to cell moving direction X. The right part of FIG. 8 is the coaxial illumination of this invention where laser propagating in the same direction of the Coulter aperture axis and cell moving direction X.

Since particle moving along entire aperture thickness (100 µm or more) coincident with laser beam propagation direction within the Rayleigh region of focused laser beam (FIG. 8 right 57A), so the interrogating time will be much longer than the interrogating time in the cross illumination scheme of the conventional flow cytometry-based systems where the particle is interrogated by the laser beam only in the cross section of the focused laser beam waist size (FIG. 8 left 56, 57 about 20 µm). The scattering signal's time width is about 5 time wider, and the requirement on detector's response time thus is eased, and larger area detector can be used, also increase the detectable angular regions. The optical sensing zone in the present invention will be the entire aperture (diameter of 50 µm to 80 µm and thickness of 100 µm) but in cross illumination the optical sensing zone is only about 20 µm or so (the focus spot size), due to the laser-particle interrogation increasing, the scattering light intensity would be at least 5 times greater in the present invention comparing to conventional flow cytometry-based systems.

Since no flow cell was used, the laser beam will not interface with the flow cell's wall and aperture's cylindrical surface where the high focused laser intensity hits the wall and the reflected light creates unwanted noise. In the present method the flow chamber window (73 in FIGS. 9 and 73A in FIG. 10) is located far from the aperture center (or the laser focused beam region, i.e. Rayleigh region of the Gaussian beam) where the laser beam has a much larger size and a much lower intensity and creates much less back reflection. The background noise thereupon is greatly reduced.

Figure 11A:
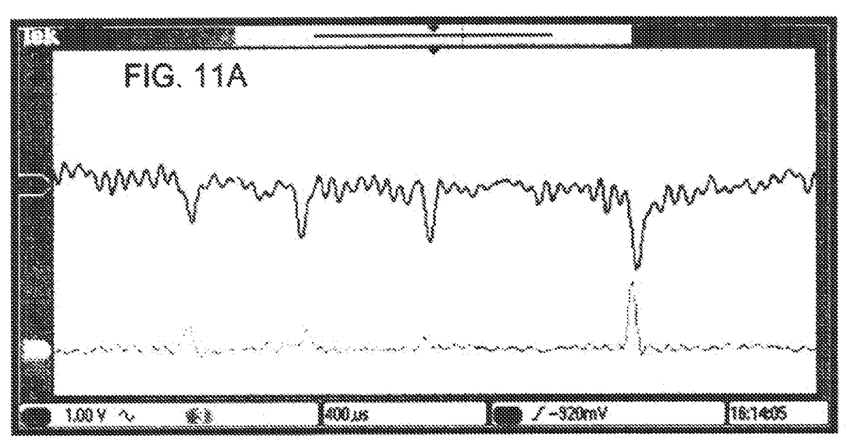
Figure 12:
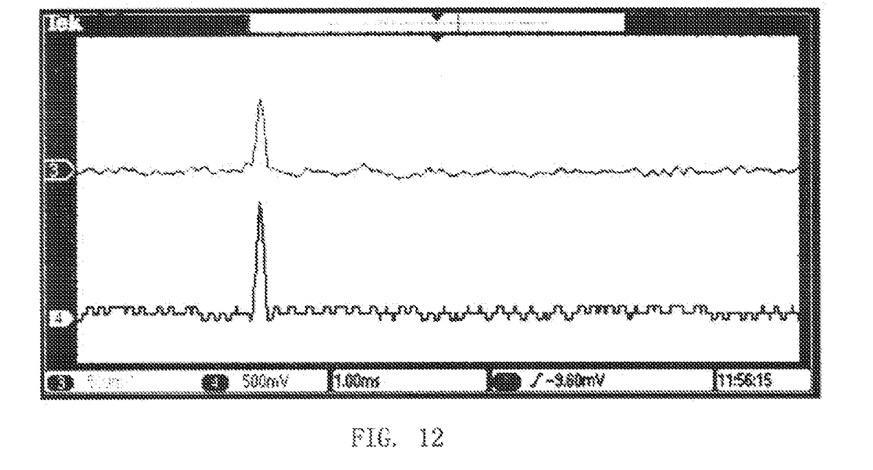
FIG. 12 is the Oscilloscope display of detected back scattering (upper track) and DC (lower track) signal of Quality control material.
Figure 13:
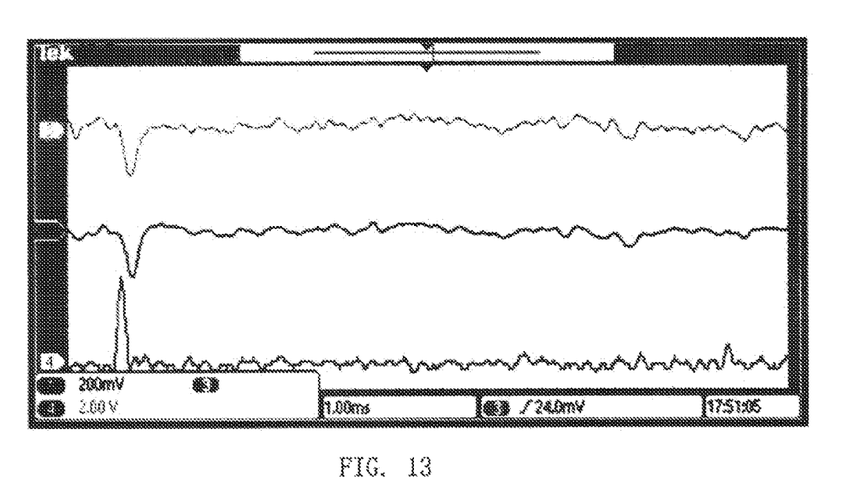
FIG. 13 is the Oscilloscope display of detected back scattering (upper track) and DC (lower track) signal of 7 µm latex particle.

The above three advantages would greatly increase the signal and reduce the noise. FIGS. 11, 12 and 13 show the forward scattering, back scattering and DC signal for 7 µm latex particle and quality control material. Note that the forward scattering has 920 mV background noise while back scattering only has 24 mV. These experimental results indicate that the back scattering signal to noise (S/N) ratio is greatly increased resulting in the higher differential power, especially due to the high backscatter S/N ratio.

Figure 9:
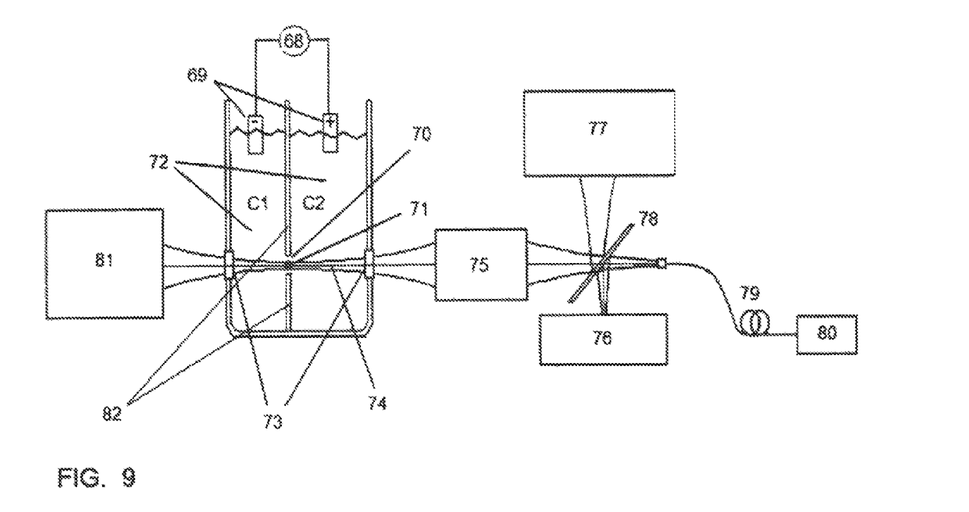
FIG. 9 is one embodiment of Coaxial illumination of Coulter aperture in 5-diff blood analyzer.
Figure 10:
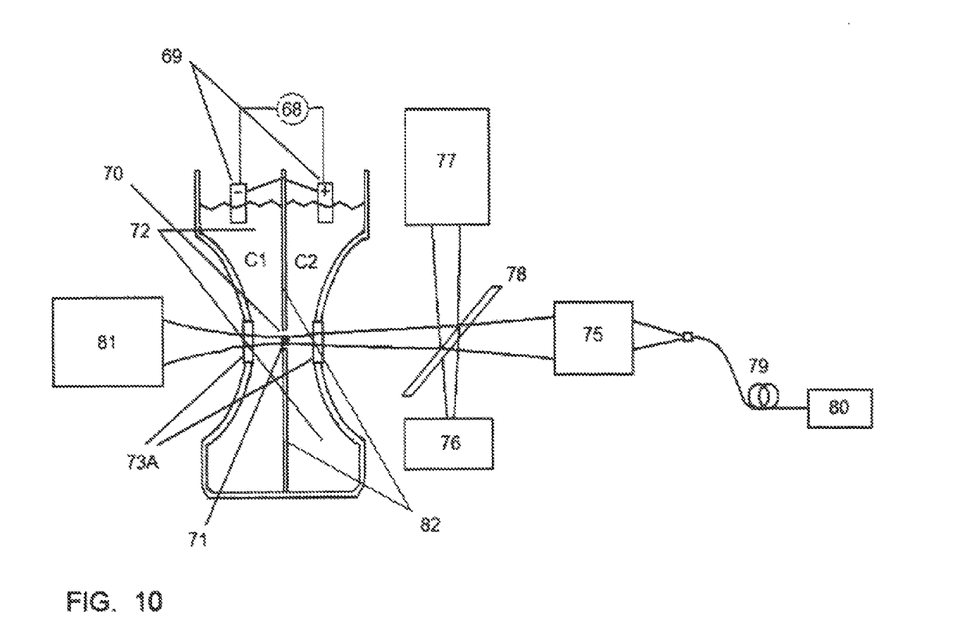
FIG. 10 similar to FIG. 9 except in FIG. 10 there is no common elements of illuminating optics and back scattering detecting optics, also in FIG. 10 the flow chamber geometry if different to FIG. 9's.

FIG. 9 is the schematic diagram of one of embodiment of present invention. It incorporates the coaxial illuminated Coulter aperture into the 5-diff differential blood analyzer. The two parts of flow chamber, C1 and C2 are separated by aperture plate 82 and connected only by the aperture 70. The aperture current 68 between two electrodes 69 was created when cell 71, suspended in saline solution 72, passes through aperture 70, one at a time. The laser 80, coupled to optical fiber 79, passes a beam splitter 78, where one part of the light is utilized to illumination optics 75 to form a focused laser beam, with beam axis 74, propagates along its axis coincident with cell moving direction inside the aperture, i.e. the axis of Coulter aperture 74. The laser beam, passing through a flow chamber window 73, is focused at the center of aperture, interacts with cell 71 and creates scattering light in both forward and back directions. The forward scatter (and axial light loss) is collected by detection optics 81 and back scatter is collected by detection optics 77 through partial reflection of the beam splitter plate 78 and illumination optics 75. The compensation optics 76 is used to follow the laser source power fluctuation. FIG. 10 is an alternative embodiment of FIG. 9. The flow chamber C1 and C2 and beam splitter plate 78 have different geometry, which can be adjusted for illumination optics 75 and detection optics 77 with no common parts contrary to FIG. 9.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed. Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are entitled.

What is claimed is:

1. A method for directly illuminating a Coulter aperture so light scattering can be incorporated into the Coulter aperture and a 5-diff blood analyzer to realize functional hematology analyzer comprising:
   providing a flow chamber which is separated into two portions by a plate having the Coulter aperture; and
   using a light source to directly coaxial illuminate the Coulter aperture with an illuminating beam;
   wherein the illuminating beam propagates in a same direction as an axis of the Coulter aperture and a cell's moving direction.

2. The method of claim 1 wherein light from the light source propagates along the axis of Coulter aperture and is focused at the center of the Coulter aperture to uniformly illuminate the Coulter aperture.

3. The method of claim 1 wherein the light source is a laser providing the illuminating beam which is focused to the center of the Coulter aperture, has a focused beam waist size less than the diameter of the Coulter aperture, and a Rayleigh region of the focused laser beam is several aperture lengths.

4. The method of claim 1 applied to a hematology instrument to perform complete blood count (CBC), white blood cell 3-part differential and other blood parameter measurements for humans or to perform analysis for other cells or to perform analysis on animal blood.

5. The method of claim 1 wherein the light source has different wavelengths for different applications.

6. The method of claim 1 wherein the light source is a laser, a light emitting diode (LED), an arc lamp, or an incandescent light source.

7. The method of claim 1 wherein a sensing zone can be the entire Coulter aperture, a front portion of the aperture, a middle portion of the aperture, a rear portion of the aperture, or a combination of the aperture portions.

8. The method of claim 5 wherein a wavelength of light from the light source can range from ultraviolet to infrared.

9. The method of claim 6 wherein the laser is a gas laser.

10. The method of claim 6 wherein the laser is a He—Ne laser, an Argon-ion laser, a diode laser, a fiber coupled diode laser, a solid state laser, a fiber coupled solid state laser, a diode pumped solid state laser, a tunable laser, or a fiber laser.

11. The method of claim 6 wherein the two portions of the flow chamber are connected by only one path through the Coulter aperture; wherein the flow chamber has two optical windows to form a light path for illumination and scattering detection; and wherein the two window's surfaces are centered at and perpendicular to a common axis of the laser beam and the Coulter aperture axis which is also the cell's moving direction.

12. The method of claim 11 wherein the optical windows are parallel optical plates of optical glass, fused silica, sapphire, or quartz or are optical lenses.

13. The method of claim 7 further comprises a signal detection system which is only sensitive to at least one spatial region of the sensing zone; wherein the scattering of a particle only within this spatial region can be detected by the detection system and any other cells outside of this spatial region, even if interrogated by a laser beam will be blocked from entering the detection system.

14. The method of claim 13 wherein the signal detection system is optical, electronic, or opto-electronic.

15. The method of claim 13 wherein the signal detection system is only sensitive to a cell within the spatial region and any reflected light background from any interface of different optical materials which is background noise will be blocked and only useful back scattering light from the cell can be detected to enhance a signal to noise ratio.

16. The method of claim 13 wherein the detection system can detect forward and back direction scattering light in different angular regions, or a combination of several angular regions.

17. The method of claim 13 wherein the signal detection system can detect single wavelength or multi-wavelength spectroscopic light in both forward and backward directions.

18. The method of claim 16 wherein forward direction signals can be forward scattering light signals or axial light loss signals.

19. The method of claim 16 wherein detectable light signals in both forward or backward directions can be single wavelength or multi-wavelength fluorescence signal, or other inelastic light scattering signals.

20. An apparatus for directly illuminating a Coulter aperture so light scattering can be incorporated into the Coulter aperture and a 5-diff blood analyzer to realize a functional hematology analyzer comprising:
   a flow chamber which is separated into two portions by a plate having the Coulter aperture; and
   a light source to directly coaxial illuminate the Coulter aperture with an illuminating beam;
   wherein the illuminating beam propagates in a same direction as an axis of the Coulter aperture and a cell's moving direction.

21. The apparatus of claim 20 wherein light from the light source propagates along the axis of Coulter aperture and is focused at the center of the Coulter aperture to uniformly illuminate the Coulter aperture.

22. The apparatus of claim 20 wherein the light source is a laser providing the illuminating beam which is focused to the center of the Coulter aperture, has a focused beam waist size less than the diameter of the Coulter aperture, and a Rayleigh region of the focused laser beam is several aperture lengths.

23. The apparatus of claim 20 coupled to a hematology instrument which performs complete blood count (CBC), white blood cell 3-part differential and other blood parameter measurements for humans or which performs analysis for other cells or which performs analysis on animal blood.

24. The apparatus of claim 20 wherein the light source has different wavelengths for different applications.

25. The apparatus of claim 20 wherein the illuminating light source is a laser, a light emitting diode (LED), an arc lamp, or an incandescent light source.

26. The apparatus of claim 20 wherein a sensing zone can be the entire Coulter aperture, a front portion of the aperture, a middle portion of the aperture, a rear portion of the aperture, or a combination of the aperture portions.

27. The apparatus of claim 24 wherein a wavelength of light from the light source can range from ultraviolet to infrared.

28. The apparatus of claim 25 wherein the laser is a gas laser.

29. The apparatus of claim 25 wherein the laser is a He—Ne laser, an Argon-ion laser, a diode laser, a fiber coupled diode laser, a solid state laser, a fiber coupled solid state laser, a diode pumped solid state laser, a tunable laser, or a fiber laser.

30. The apparatus of claim 25 wherein the two portions of the flow chamber are connected by only one path through the Coulter aperture; wherein the flow chamber has two optical windows to form a light path for illumination and scattering detection; and wherein the two window's surfaces are centered at and perpendicular to a common axis of the laser beam and the Coulter aperture axis which is also the cell's moving direction.

31. The apparatus of claim 30 wherein the optical windows are parallel optical plates of optical glass, fused silica, sapphire, or quartz or are optical lenses.

32. The apparatus of claim 26 further comprises a signal detection system which is only sensitive to at least one spatial region of the sensing zone.

33. The apparatus of claim 32 wherein the signal detection system is optical, electronic, or opto-electronic.

34. The apparatus of claim 32 wherein the signal detection system is only sensitive to a cell within the spatial region and any reflected light background from any interface of different optical materials which is background noise will be blocked and only useful back scattering light from the cell can be detected to enhance a signal to noise ratio.

35. The apparatus of claim 32 wherein the signal detection system can detect single wavelength or multi-wavelength spectroscopic light in both forward and backward directions.

36. The apparatus of claim 32 wherein the detection system can detect forward and back direction scattering light in different angular regions, or a combination of several angular regions.

37. The apparatus of claim 36 wherein forward direction signals can be forward scattering light signals or axial light loss signals.

38. The apparatus of claim 36 wherein detectable light signals in both forward or backward directions can be single wavelength or multi-wavelength fluorescence signal, or other inelastic light scattering signals.

* * * * *